United States Patent
Kamijo

(10) Patent No.: US 7,569,825 B2
(45) Date of Patent: Aug. 4, 2009

(54) INSPECTION DEVICE

(75) Inventor: Hideaki Kamijo, Tokyo (JP)

(73) Assignee: Nidec Copal Corporation, Tokyo (JP)

( * ) Notice: Subject to any disclaimer, the term of this patent is extended or adjusted under 35 U.S.C. 154(b) by 397 days.

(21) Appl. No.: 10/597,632

(22) PCT Filed: Feb. 3, 2005

(86) PCT No.: PCT/JP2005/001573

§ 371 (c)(1),
(2), (4) Date: Aug. 2, 2006

(87) PCT Pub. No.: WO2005/078670

PCT Pub. Date: Aug. 25, 2005

(65) Prior Publication Data

US 2008/0259314 A1    Oct. 23, 2008

(30) Foreign Application Priority Data

Feb. 12, 2004    (JP)    ............................. 2004-035466

(51) Int. Cl.
*G01J 5/00* (2006.01)
(52) U.S. Cl. .............................. 250/360.1; 250/339.05; 250/358.1; 250/359.1
(58) Field of Classification Search .............. 250/358.1, 250/359.1, 360.1, 339.05
See application file for complete search history.

(56) References Cited

U.S. PATENT DOCUMENTS

| | | | |
|---|---|---|---|
| 5,413,098 A * | 5/1995 | Benaron | ...................... 600/310 |
| 6,730,911 B2 | 5/2004 | Uemura et al. | |
| 6,731,384 B2 * | 5/2004 | Ohshima et al. | ......... 356/237.2 |
| 2003/0042438 A1 * | 3/2003 | Lawandy et al. | ............ 250/556 |
| 2003/0197866 A1 | 10/2003 | Uemura et al. | |
| 2004/0021064 A1 * | 2/2004 | Baudat | ...................... 250/239 |

FOREIGN PATENT DOCUMENTS

| | | |
|---|---|---|
| CN | 1381714 A | 11/2002 |
| JP | 2002-074450 | 3/2002 |
| JP | 2003-315260 | 11/2003 |
| WO | WO 94/16412 | 7/1994 |

* cited by examiner

Primary Examiner—David P Porta
Assistant Examiner—Mark R Gaworecki
(74) Attorney, Agent, or Firm—Leydig, Voit & Mayer, Ltd.

(57) ABSTRACT

An inspection device includes a light source emitting ultraviolet light onto a banknote conveyed on a conveyance path, a light source emitting infrared light onto the banknote, a photosensor for detecting light from the banknote, a light source control processing portion for controlling the light sources while individually switching the light sources at high speed, and a discrimination processing portion. The discrimination processing portion first imports each of two detection signals (output signals) from the photosensor, which are obtained by substantially within an identical period of time when the banknote is illuminated with the light through sequential lighting of the light sources and calculates an output ratio of the photosensor. Then the calculated output ratio of the photosensor is compared and collated with reference data preliminarily stored in a memory, determining authenticity and denomination of the banknote.

13 Claims, 14 Drawing Sheets

(a) LIGHTING TIMING OF LIGHT SOURCE 12A (b) LIGHTING TIMING OF LIGHT SOURCE 12B

INSPECTION DEVICE

TECHNICAL FIELD

The present invention relates to an inspection device for performing inspection, such as determination on authenticity or denominations of banknotes, chits and the like passing on a conveyance path.

BACKGROUND ART

One of the known inspection device for inspecting sheets such as banknotes is an apparatus provided with a photosensor for measuring reflection on surfaces of the sheets, and an illumination portion for illuminating the sheets with light, and arranged to discriminate denominations or authenticity of the sheets, for example, as described in Patent Document 1.

Patent Document 1: Japanese Patent Application Laid-Open No. 2002-74450

DISCLOSURE OF THE INVENTION

Problem to be Solved by the Invention

In recent years, the banknotes and others are sometimes provided with two or more types of characteristic patterns for security, as countermeasures against forgery of the banknotes, stock certificates, and so on. In this case, it is necessary to accurately discriminate such characteristic patterns and to perform the denomination determination or authenticity determination of the banknotes and others with high accuracy.

An object of the present invention is to provide an inspection device capable of achieving improvement in accuracy of recognition of an object.

Means for Solving the Problem

The present invention is an inspection device for inspecting an object passing on a conveyance path, comprising: an illumination portion for illuminating the object with light in a plurality of wavelength bands; at least one light-receiving and detecting element for receiving light generated from the object; and a discrimination processing portion for discriminating the object by combining data of a plurality of detection signals obtained by the light-receiving and detecting element which receives the light generated from the object substantially within an identical period of time when the illuminating portion illuminates the object with the light in the plurality of wavelength bands, and by comparing and collating combined data with preset reference data.

In this inspection device, when the object passing on the conveyance path arrives at a predetermined location, the illumination portion illuminates the object with the light in the plurality of wavelength bands and the light-receiving and detecting element receives the light generated from the object upon the illumination. The object generates lights different corresponding to the light beams in the plurality of wavelength bands emitted from the illumination portion. For this reason, the detection signals by the light-receiving and detecting element are a plurality of detection signals corresponding to the light beams in the plurality of wavelength bands. Since these detection signals are signals obtained by receiving the light generated from the object substantially within an identical period of time upon irradiation of the object with the light beams in the plurality of wavelength bands, they are detection signals from one arbitrary region of the object. Then the discrimination processing portion performs the discrimination process of the object by generating the combined data from the plurality of detection signals and by comparing and collating the combined data with the reference data. When the apparatus is constructed by adopting this technique and when the apparatus is applied, for example, to a case where the object is provided with two or more types of characteristic patterns to generate a plurality of light components in different wavelength bands with reception of the light emitted from the illumination portion, the apparatus is able to accurately discriminate these characteristic patterns even in that case. This improves the accuracy of recognition of the object.

Preferably, the discrimination processing portion obtains, as the combined data, a ratio of a plurality of detected values obtained by the light-receiving and detecting element which receives the light generated from the object substantially within an identical period of time when the illuminating portion illuminates the object with the light in the plurality of wavelength bands. If vertical motion (conveyance fluttering) of the object occurs during passage of the object on the conveyance path, the illumination position on the object upon irradiation of the object with the light from the illumination portion will deviate in the height direction, so as to cause variation of values detected by the light-receiving and detecting element. However, even if the conveyance fluttering of the object occurs, the plurality of detection signals corresponding to the light beams in the plurality of wavelength bands are those detected in a state in which the object is located substantially at the same conveyance height position, when the light-receiving and detecting element receives the light generated from the object, substantially within the identical period of time. On the other hand, the ratio of the plurality of detected values obtained by receiving the lights generated from the object, substantially within the identical period of time by the light-receiving and detecting element is always almost constant, irrespective of the conveyance height position of the object. Therefore, with focus on this point, the ratio of the plurality of detected values is used as the combined data, whereby the discrimination of the object can be performed, without being affected by the variation of the detected values by the light-receiving and detecting element, even if the conveyance fluttering of the object occurs. This further improves the accuracy of recognition of the object.

Preferably, the illumination portion includes a plurality of light sources for emitting light beams in different wavelength bands, and a lighting control portion for performing control to light each of the light sources while individually switching the light sources. In this configuration, the plurality of light sources are lighted while being switched at high speed, and one light-receiving and detecting element receives lights generated from the object upon the lighting, in order, whereby the apparatus is able to securely receive substantially within the identical period of time the lights generated from the object upon the irradiation of the object with the light beams in the plurality of wavelength bands. In this case, the apparatus needs only one light-receiving and detecting element to be used, and it is thus feasible to achieve reduction of cost of parts.

The illumination portion may include a plurality of light sources for emitting respective light beams in different wavelength bands, and a plurality of light-receiving and detecting elements may be separately provided to receive light generated from the object in correspondence to the respective light sources when the object is illuminated with the light beams from the respective light sources. In this configuration, for example, when the object passing on the conveyance path arrives at a predetermined location, all the light sources are constantly kept lighting. Then the separate light-receiving and detecting elements receive at the same timing the respective lights, corresponding to the respective light sources, generated from the object at that time, whereby the apparatus is able to securely receive substantially within the same period of time the lights generated from the object upon irradiation of the object with the light beams in the plurality of wavelength bands. In this case, it becomes feasible to achieve reduction in influence of noise produced upon lighting of the light sources and to stabilize the light emission levels of the light sources. In addition, it is easy to perform the control of lighting of the light sources.

In this connection, the device further comprises optical filters each of which is disposed between the conveyance path and each light-receiving and detecting element, and each of which is configured to transmit only a certain light component among light components with a plurality of features generated from the object when the object is illuminated with the light from each light source. In this case, the apparatus is able to prevent a light component with the same feature generated from the object, from entering the plurality of light-receiving and detecting elements. Since this securely suppresses crosstalk of light for each light-receiving and detecting element even in the case where the plurality of light-receiving and detecting elements are arranged in proximity in order to achieve miniaturization or the like of the inspection device, each light-receiving and detecting element can be prevented from receiving an unwanted light component as noise. The light components with features generated from the object include a fluorescent component generated upon irradiation of the object with ultraviolet light, a reflected component upon irradiation of the object with infrared light, and so on.

Furthermore, preferably, the plurality of light sources include a first light source for emitting ultraviolet light, and a second light source for emitting infrared light. This configuration permits the apparatus to detect a level of fluorescence generated in the object upon irradiation of the object with ultraviolet light, and a level of infrared light reflected on the object upon irradiation of the object with infrared light.

In this connection, an ultraviolet removing filter is preferably disposed between the conveyance path and the light-receiving and detecting element and is configured to remove the ultraviolet light emitted from the first light source. This permits the apparatus to prevent the ultraviolet light emitted from the first light source, from entering the light-receiving and detecting element, as noise.

In addition, preferably, an ultraviolet-infrared transmitting filter is disposed between the conveyance path, the first light source and the second light source, and is configured to remove a visible light component in the ultraviolet light emitted from the first light source and to transmit the infrared light emitted from the second light source. This permits the apparatus to prevent the visible light component in the ultraviolet light emitted from the first light source, from entering the light-receiving and detecting element, as noise.

Furthermore, preferably, the plurality of light sources include a first light source for emitting ultraviolet light, a second light source for emitting infrared light, and a third light source for emitting green light. This permits the apparatus to achieve improvement in the accuracy of recognition of the object because a detection signal upon irradiation with the green light is also added to the discrimination of the object.

EFFECT OF THE INVENTION

The present invention enables accurate recognition of authenticity or the like of the object passing on the conveyance path. This enables the apparatus to well handle even highly accurately forged objects.

DESCRIPTION OF REFERENCE SYMBOLS

1 inspection device; 2 conveyance path; 3 banknote (object); 7 sensor unit; 8 control unit; 12A light source (first light source, illumination portion); 12B light source (second light source, illumination portion); 16 ultraviolet-infrared transmitting filter; 17 photosensor; 17A, 17B photosensors; 18 condenser lens (ultraviolet removing filter); 20 light source control processing portion (illumination portion); 21 memory portion; 22 discrimination processing portion; 30 inspection device; 31 sensor unit; 32 control unit; 35 visible light transmitting filter (optical filter); 36 infrared transmitting filter (optical filter); 37 light source control processing portion (illumination portion); 38 memory portion; 39 discrimination processing portion.

BEST MODE FOR CARRYING OUT THE INVENTION

A preferred embodiment of the inspection device according to the present invention will be described below in detail with reference to the drawings.

Figure 1:
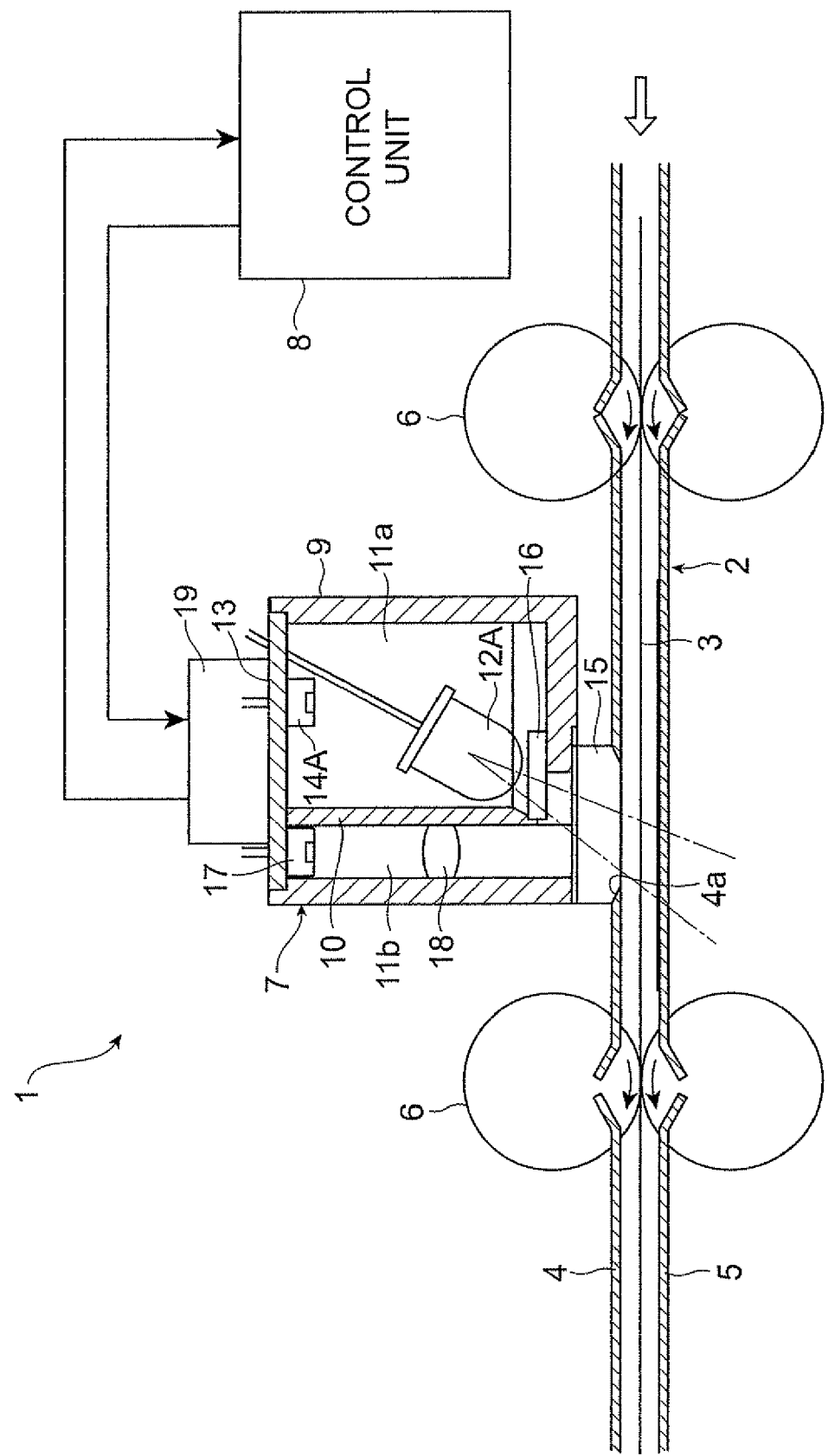
FIG. 1 is a configuration diagram showing a first embodiment of an inspection device according to the present invention.

FIG. 1 is a configuration diagram showing the first embodiment of an inspection device according to the present invention. As shown in the drawing, the inspection device 1 of the present embodiment is an apparatus for carrying out the authenticity determination and the denomination determination of banknote 3 passing on a conveyance path 2, and is incorporated, for example, in a banknote counter. The banknote 3 contains infrared ink to reflect infrared light (IR light), and fluorescent ink to generate fluorescence with reception of ultraviolet light (UV light), as characteristic patterns for security effective as countermeasures against forgery.

The conveyance path 2 includes an upper conveyance guide plate 4 with an aperture 4a, and a lower conveyance guide plate 5. In order to convey the banknote 3 smoothly, a clearance of about 2-3 mm is provided between the upper conveyance guide plate 4 and the lower conveyance guide plate 5. A plurality of conveyance rollers 6 for conveying the banknote 3 in a direction of an arrow are disposed midway of the conveyance path 2.

The inspection device 1 has a sensor unit 7 disposed above the upper conveyance guide plate 4, and a control unit 8 connected to this sensor unit 7. The sensor unit 7 has a housing 9 of approximately rectangular parallelepiped shape, and a partition 10 extending along the direction of height is provided in this housing 9.

Figure 2:
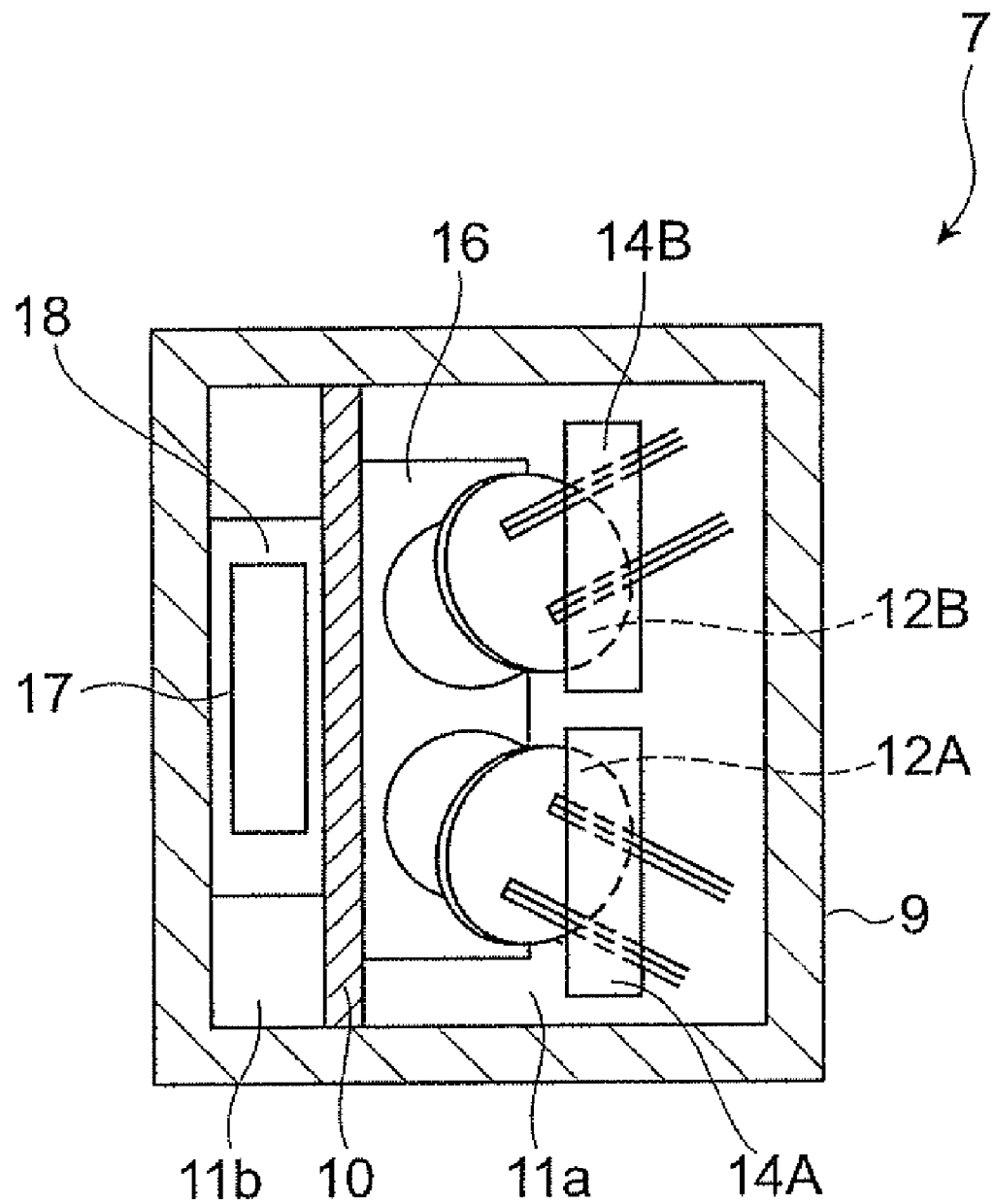
FIG. 2 is a horizontal sectional view of a housing shown in FIG. 1.

Two light sources 12A, 12B for emitting light onto the surface of the banknote 3 conveyed on the conveyance path 2 are accommodated, as shown in FIG. 2, in one space 11a of the housing 9 formed by partition 10. The light source 12A is an ultraviolet LED for generating light containing an ultraviolet component (in the band of about 200-400 nm), and the light source 12B is an infrared LED for generating light containing an infrared component (in the band of about 780-1400 nm). The light sources 12A, 12B are arranged alongside so as to emit light toward a substantially identical location on the banknote 3 and are fixed to a printed circuit board 13 provided on an upper surface portion of the housing 9.

Monitor photosensors 14A, 14B, which monitor the quantity of light emitted from the light sources 12A, 12B, are mounted on the printed circuit board 13. The photosensors 14A, 14B are light-receiving and detecting elements, for example, such as photodiodes or phototransistors.

A dustproof glass plate 15 is fixed to the lower portion of this housing 9. The dustproof glass plate 15 is made of a material with an extremely high transmittance for ultraviolet light and infrared light. The lower surface portion of the dustproof glass plate 15 is fixed to the aperture 4a of the conveyance path 2.

An ultraviolet-infrared transmitting filter 16 is disposed between the dustproof glass plate 15 and the light sources 12A, 12B. The ultraviolet-infrared transmitting filter 16 is an optical filter that removes the visible light component (in the band of about 380 to 780 nm) contained in the light emitted from the light source 12A and that transmits the infrared light emitted from the light source 12B. When the apparatus is provided with such ultraviolet-infrared transmitting filter 16, the apparatus is able to prevent the visible light component from being reflected on the surface of the banknote 3 and becoming unwanted noise.

A photosensor 17 for detection, which receives light generated from the surface of the banknote 3 upon irradiation of the surface of the banknote 3 with the light from the light sources 12A, 12B, is accommodated in the other space 11b of the housing 9 created by the partition 10. The photosensor 17 is a light-receiving and detecting element, for example, such as a photodiode or a phototransistor, and is fixed to the printed circuit board 13.

A condenser lens 18 having an ultraviolet removing filter function for removing ultraviolet light is disposed between the dustproof glass plate 15 and the photosensor 17. In this configuration, the light emitted from the surface of the banknote 3 passes through the condenser lens 18 to enter the photosensor 17. At this time, the ultraviolet removing filter function of the condenser lens 18 prevents the photosensor 17 from receiving the ultraviolet light emitted from the light source 12A, as noise.

An electronic circuit component (not shown) and a connector 19 for connection to outside are mounted, in addition to the light sources 12A, 12B, photosensor 17, etc., on the printed circuit board 13. The aforementioned control unit 8 is connected through an electric cable to the connector 19 for connection to outside.

Figure 3:
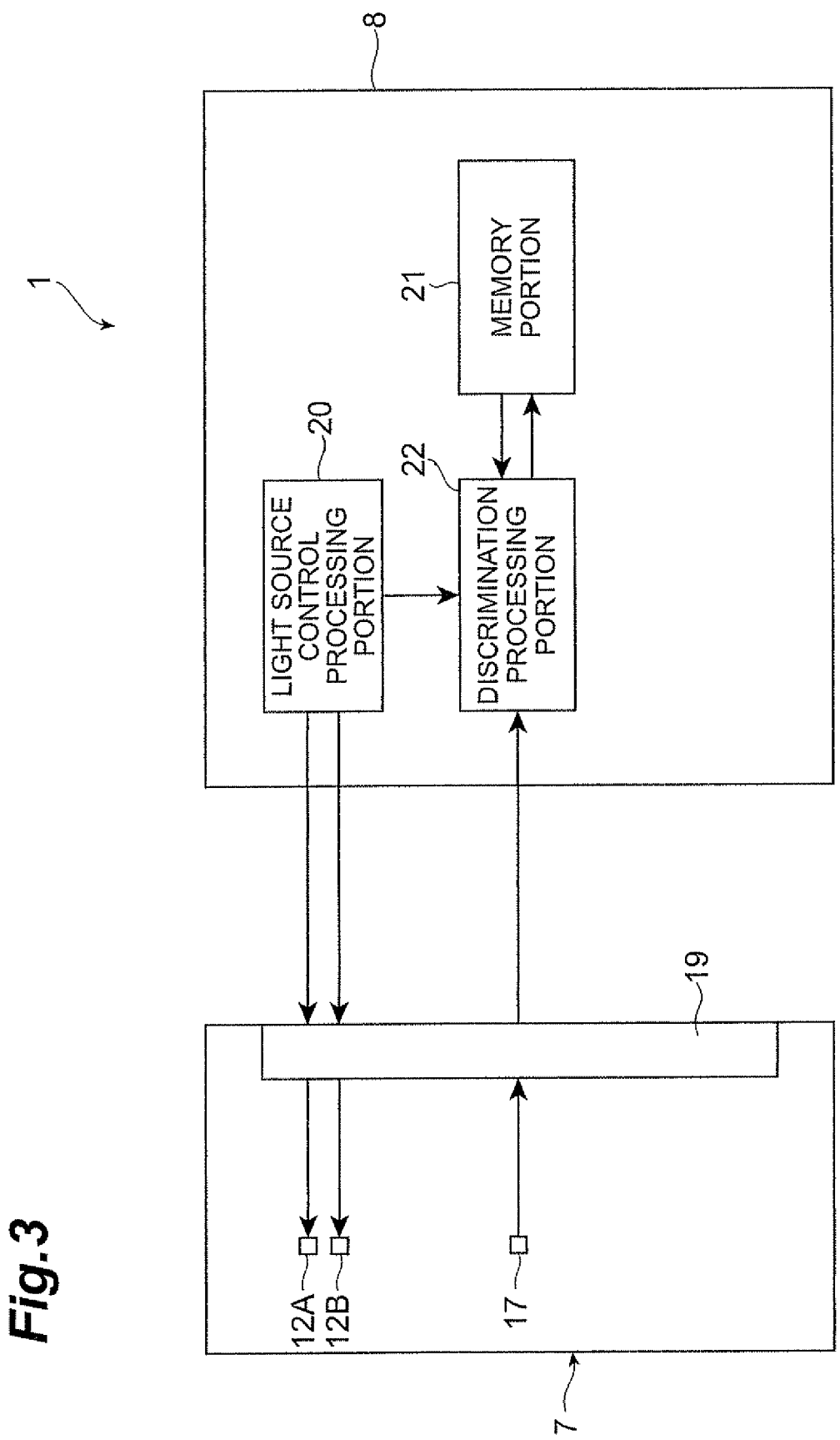
FIG. 3 is a diagram showing functional blocks of a control unit shown in FIG. 1.

The control unit 8, as shown in FIG. 3, has a light source control processing portion 20, a memory portion 21, and a discrimination processing portion 22 (discriminating means). The light sources 12A, 12B and the light source control processing portion 20 constitute an illumination portion (illuminating means) for illuminating the banknote 3.

Figure 4:
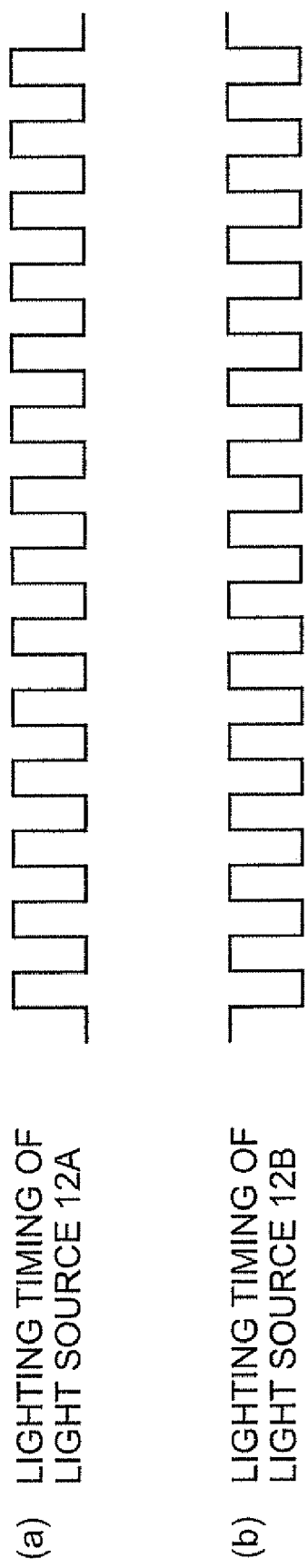
FIG. 4 is a chart showing lighting timings of two light sources shown in FIG. 2.

When a banknote arrival sensor (not shown) detects arrival of a banknote 3 passing on the conveyance path 2 in the area near the aperture 4a of the upper conveyance guide plate 4, the light source control processing portion 20 sends a control signal to a light source driving circuit (not shown) constituting a lighting control portion and mounted on the printed circuit board 13 of the sensor unit 7, to individually control each of the light sources 12A, 12B. At this time, the light source control processing portion 20 performs such control as to light the light sources 12A, 12B while individually switching them at high speed, as shown in FIG. 4. The lighting switch period of the light sources 12A, 12B is, for example, approximately 1-10 ms.

Reference data for discrimination of banknote is preliminarily stored in the memory portion 21. The reference data to be used is a ratio of output value (detected value) $P_1$ from the photosensor 17 obtained by receiving light upon irradiation with the light from the light source 12A and output value $P_2$ from the photosensor 17 obtained by receiving light upon irradiation with the light from the light source 12B (hereinafter referred to as an output ratio of photosensor 17), for a plurality of inspection regions in the longitudinal direction of banknote 3. The reference data of the output ratio of photosensor 17 is obtained from detected values $P_1$, $P_2$ of photosensor 17 obtained by sequentially receiving light upon switched lighting of the light sources 12A, 12B as described above with a real banknote 3 being conveyed on the conveyance path 2. Since the lighting of the light sources 12A, 12B is switched at high speed, the detected values $P_1$, $P_2$ of photosensor 17 upon irradiation with the light from the light sources 12A, 12B are values obtained by reception of light substantially within an identical period of time.

Figure 5:
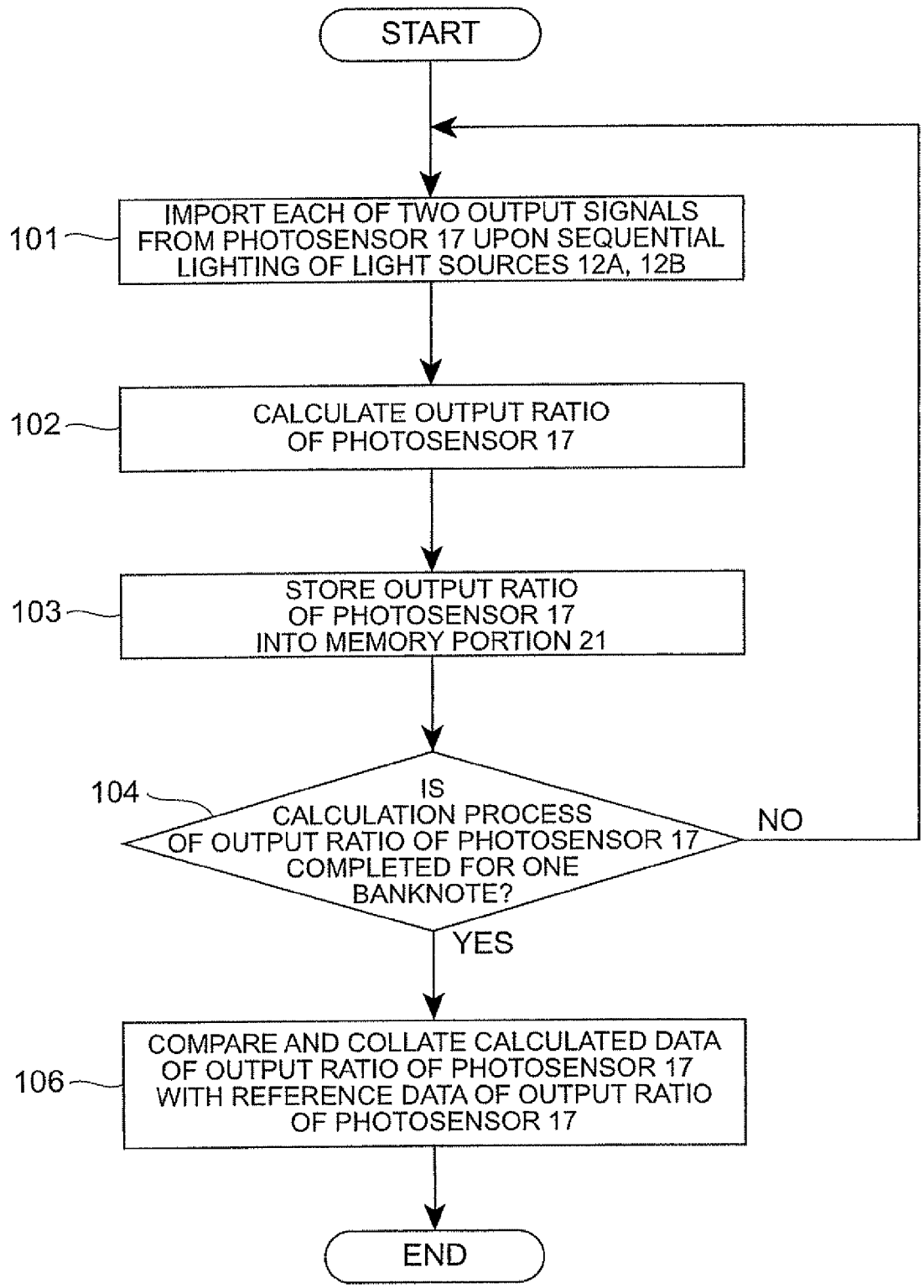
FIG. 5 is a flowchart showing a detailed processing procedure of a discrimination processing portion shown in FIG. 3.

At this time, the quantity of light from the light source (infrared LED) 12B is so set that an output value (output voltage) of photosensor 17 upon irradiation on a non-printed region in the banknote 3 becomes a voltage (e.g., 4 V) close to an output saturation level of photosensor 17. Furthermore, the quantity of light from the light source (ultraviolet LED) 12A is so set that an output voltage of photosensor 17 upon irradiation on a non-printed region in the banknote 3 becomes a voltage (e.g., 1 V) close to a low level of photosensor 17. The discrimination processing portion 22 imports detection signals (output signals) from photosensor 17, performs a predetermined operation, and discriminates the banknote 3 with the use of the reference data for discrimination of banknote stored in the memory portion 21. The detailed processing procedure of this discrimination processing portion 22 is shown in FIG. 5.

As shown in the drawing, the light sources 12A, 12B are first lighted in order to illuminate the banknote 3 under conveyance with light, and the discrimination processing portion 22 imports each of two detection signals from photosensor 17 obtained by receiving light upon irradiation of the banknote 3 with the light (step 101). Since the lighting of the light sources 12A, 12B is switched at high speed by the light source control processing portion 20 as described above, the two detection signals from photosensor 17 corresponding to the light sources 12A, 12B are signals obtained by receiving the light substantially within an identical period of time.

Subsequently, the discrimination processing portion 22 calculates the output ratio of photosensor 17 from the detected values $P_1$, $P_2$ of photosensor 17 at this timing (step 102). Then the discrimination processing portion 22 stores the output ratio of photosensor 17 thus calculated, into the memory portion 21 (step 103).

Subsequently, the discrimination processing portion 22 determines whether the output ratio of photosensor 17 has been calculated for all the inspection regions of one banknote 3 (step 104). When the output ratio of photosensor 17 is not calculated for all the regions, the above steps 101 to 103 are repeated. On the other hand, when the output ratio of photosensor 17 is calculated for all the regions, the discrimination processing portion 22 reads all the calculated data of output ratios of photosensor 17 and the reference data out of the memory portion 21 and compares and collates each calculated data with the reference data to determine the authenticity and denomination of the banknote 3 (step 105).

Figure 6:
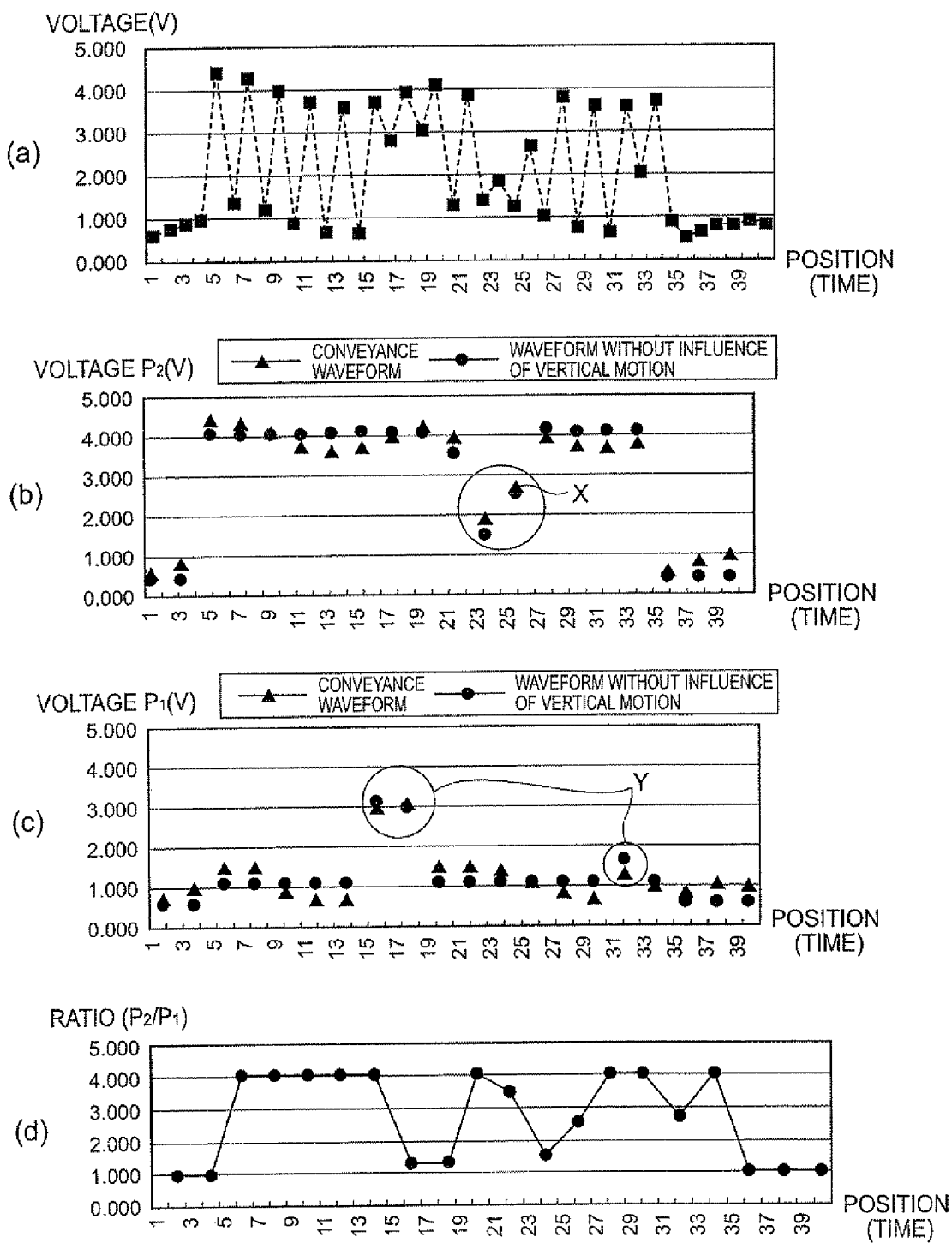
FIG. 6 is a drawing showing modeled diagrams of output value data from a photosensor obtained by receiving light upon irradiation of a banknote with light from the two light sources shown in FIG. 2, and output ratio data of the photosensor.

FIG. 6 shows modeled diagrams of output value data of photosensor 17 obtained by receiving light upon irradiation of banknote 3 with switched lighting of the light sources 12A, 12B, and output ratio data of photosensor 17 calculated from the output value data.

FIG. 6 (a) shows the output value data of photosensor 17 with the banknote 3 being conveyed on the conveyance path 2. Triangle marks in FIG. 6 (b) indicate only the output values $P_2$ of photosensor 17 obtained by receiving light upon irradiation of the banknote 3 with the infrared light from the light source 12B, out of the output value data shown in FIG. 6 (a). Triangle marks in FIG. 6 (c) indicate only the output values $P_1$ of photosensor 17 obtained by receiving light upon irradiation of the banknote 3 with the ultraviolet light from the light source 12A, out of the output value data shown in FIG. 6 (a). Black circle marks in FIGS. 6 (b) and (c) indicate the output value data of photosensor 17 in the case where the banknote 3 is assumed not to undergo vertical motion (conveyance fluttering), for reference. However, there is the predetermined clearance provided between the upper conveyance guide plate 4 and the lower conveyance guide plate 5 forming the conveyance path 2, as described above, and therefore the banknote 3 often undergoes vertical motion (conveyance fluttering) during practical conveyance of banknote 3. In this case, the output values of photosensor 17 vary, as indicated by the triangle marks in FIGS. 6 (b) and (c).

Part X in FIG. 6 (b) is a characteristic portion upon irradiation of the banknote 3 with the infrared light from the light source 12B. When the infrared light impinges upon the infrared ink which is one of characteristic patterns given to the banknote 3, the infrared light is reflected on the infrared ink, so as to change the output value of photosensor 17. The output value of photosensor 17 becomes lower in part X of this feature than in the other part. Part Y in FIG. 6 (c) represents characteristic portions upon irradiation of the banknote 3 with the ultraviolet light from the light source 12A. When the ultraviolet light impinges upon the fluorescent ink being another characteristic pattern given to the banknote 3, the fluorescent ink generates fluorescence, so as to change the output value of photosensor 17. The output value of photosensor 17 becomes higher in part Y of this feature than in the other part.

FIG. 6 (d) shows data of the output ratio ($P_2/P_1$) of photosensor 17 obtained from adjacent output values $P_1$, $P_2$ of photosensor 17 shown in FIG. 6 (a). The adjacent output values $P_1$, $P_2$ of photosensor 17 are values obtained by detecting light from the same inspection region of banknote 3 substantially within the same period of time. Namely, the adjacent output values $P_1$, $P_2$ of photosensor 17 are values obtained when the banknote 3 is located approximately at the same conveyance height position. The output ratio of photosensor 17 obtained at that time is always almost constant, irrespective of the conveyance height position of banknote 3. Therefore, there is little variation in the output ratio of photosensor 17, even with variation in the output of photosensor 17 due to the conveyance fluttering of the banknote 3.

In the present embodiment, as described above, the banknote 3 is alternately irradiated with the light beams from the two types of light sources 12A, 12B, and the discrimination of banknote 3 is carried out by retrieving the two output signals from photosensor 17 obtained by receiving light generated from the banknote 3 at that time, calculating the output ratio of photosensor 17 from the output signals, and comparing and collating the output ratio with the reference data; therefore, even in the case where the banknote 3 is provided with two types of characteristic patterns for security, the inspection device is able to accurately determine the presence/absence, positions, levels, etc. of such characteristic patterns. The apparatus is also able to determine a difference in quality of paper of banknote 3 or the like, in addition to the characteristic patterns. Furthermore, since the discrimination of banknote 3 is carried out using the output ratio of photosensor 17, the discrimination can be performed without being affected by conveyance fluttering of banknote 3. For this reason, it is also feasible, for example, to highly accurately perform discrimination of banknote 3 with a low-contrast printed pattern or the like. Since the above improves the accuracy of recognition of banknote 3, it is also feasible to perform secure determination on the authenticity or the like of counterfeit banknotes produced with recently accuracy-enhanced copiers or the like.

Though only one photosensor 17 is used, the switched lighting of the two light sources 12A, 12B permits the photosensor 17 to receive the light generated from the banknote 3 upon irradiation of banknote 3 with ultraviolet light and the light generated from the banknote 3 upon irradiation of banknote 3 with infrared light, substantially within the same period of time. For this reason, it becomes feasible to minimize the number of parts.

Figure 7:
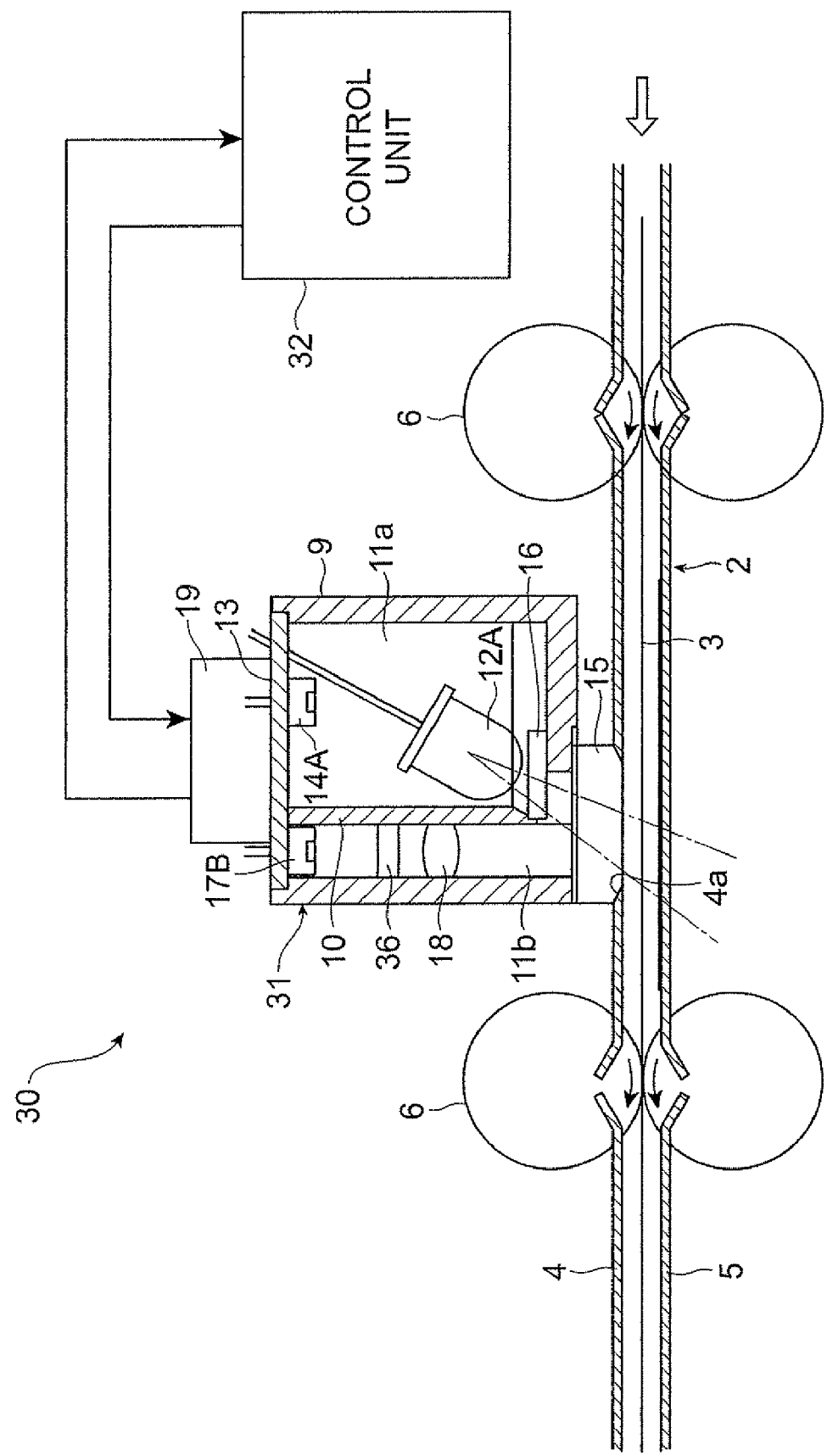
FIG. 7 is a configuration diagram showing a second embodiment of an inspection device according to the present invention.

FIG. 7 is a configuration diagram showing the second embodiment of an inspection device according to the present invention. Identical or equivalent members in the drawing will be denoted by the same reference symbols as those in the first embodiment, without redundant description thereof.

Figure 8:
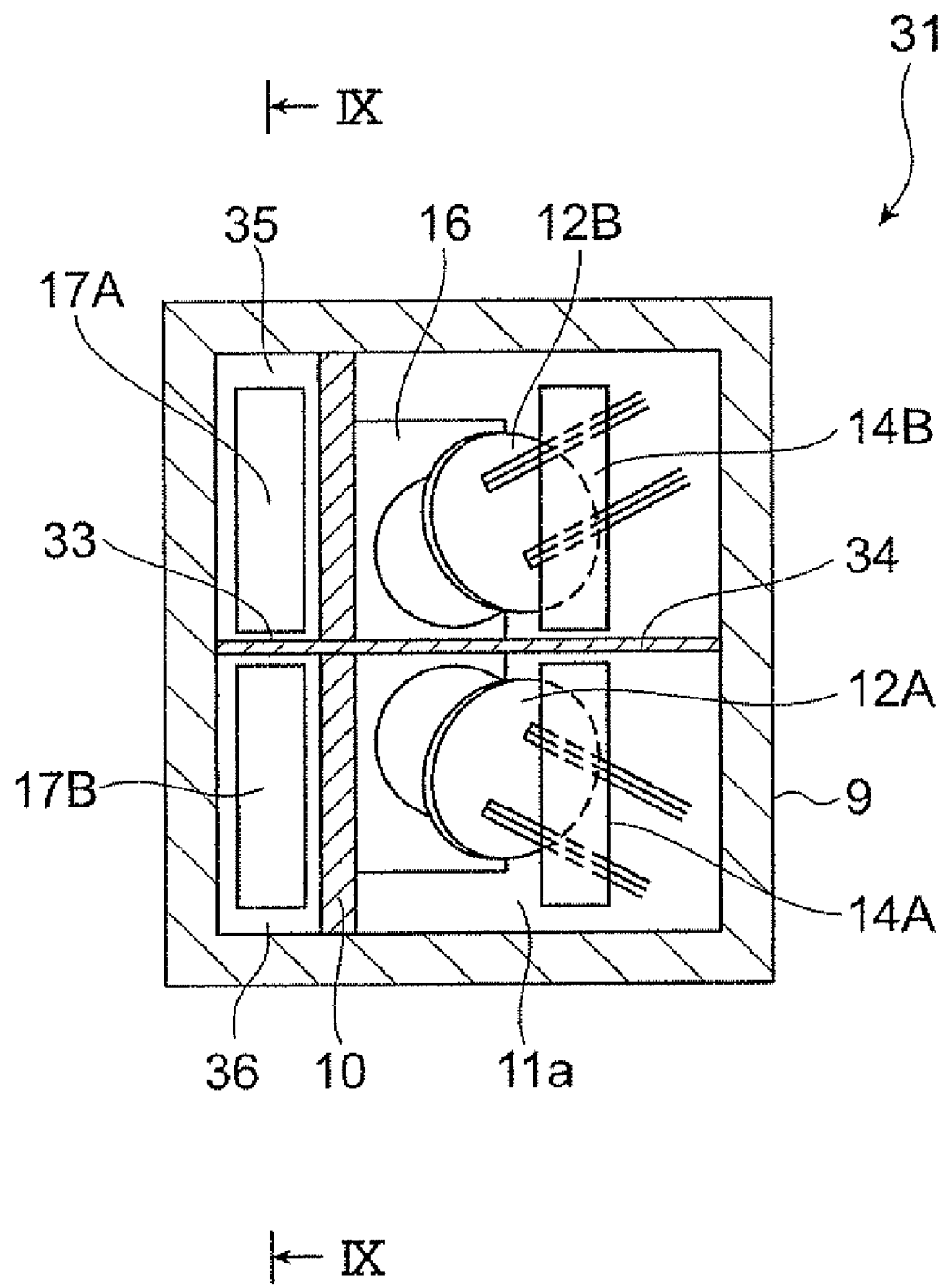
FIG. 8 is a horizontal sectional view of a housing shown in FIG. 7.
Figure 9:
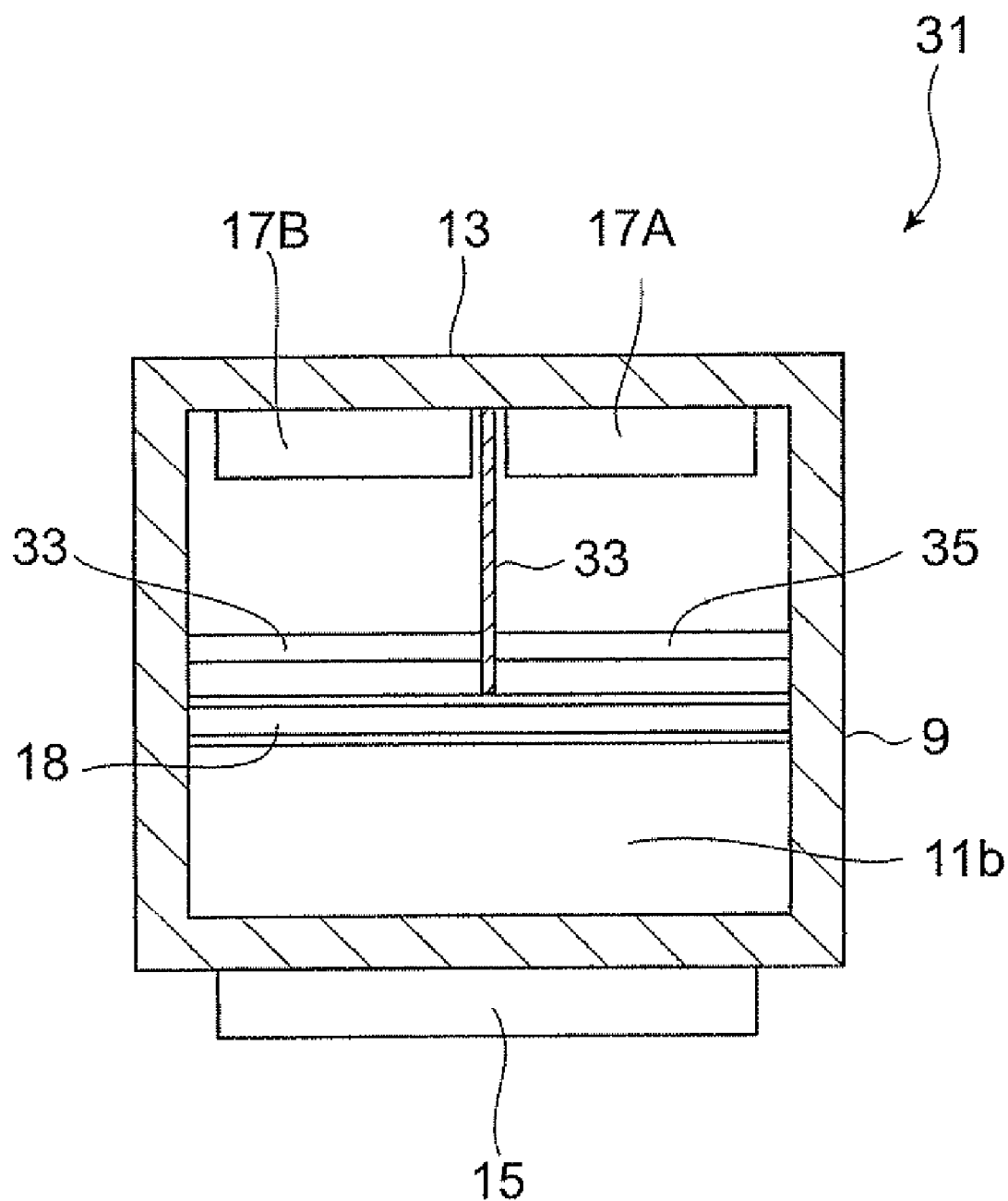
FIG. 9 is a sectional view along line IX-IX in FIG. 8.

The inspection device 30 of the present embodiment has a sensor unit 31 and a control unit 32, in place of the sensor unit 7 and control unit 8 in the first embodiment. Two photosensors 17A, 17B are accommodated alongside, as shown in FIGS. 8 and 9, in the space 11b of housing 9 in the sensor unit 31. The photosensor 17A is located so as to receive light generated from banknote 3 upon irradiation of banknote 3 with the ultraviolet light from the light source 12A, and the photosensor 17B is located so as to receive light generated from banknote 3 upon irradiation of banknote 3 with the infrared light from the light source 12B.

A partition 33, which extends in the direction of height from the printed circuit board 13 to the condenser lens 18, is provided in the space 11b of housing 9. The photosensors 17A, 17B are arranged with the partition 33 in between. A partition 34 is provided corresponding to the partition 33 and between the light sources 12A, 12B, in the space 11a of housing 9.

A visible light transmitting filter 35 is situated between the photosensor 17A and the condenser lens 18. This visible light transmitting filter 35 is an optical filter that transmits fluorescence (visible light) generated in the banknote 3 upon irradiation of banknote 3 with the ultraviolet light from the light source 12A and that removes infrared light reflected on the banknote 3 upon irradiation of banknote 3 with the infrared light from the light source 12B. An infrared transmitting filter 36 is situated between the photosensor 17B and the condenser lens 18. This infrared transmitting filter 36 is an optical filter that transmits the infrared light reflected on the banknote 3 upon irradiation of the banknote 3 with the infrared light from the light source 12B and that removes the fluorescence generated in the banknote 3 upon irradiation of banknote 3 with the ultraviolet light from the light source 12A, and reflected light of the ultraviolet light. When the apparatus is provided with such visible light transmitting filter 35 and infrared transmitting filter 36, it is feasible to securely suppress crosstalk of light for the photosensors 17A, 17B.

Figure 10:
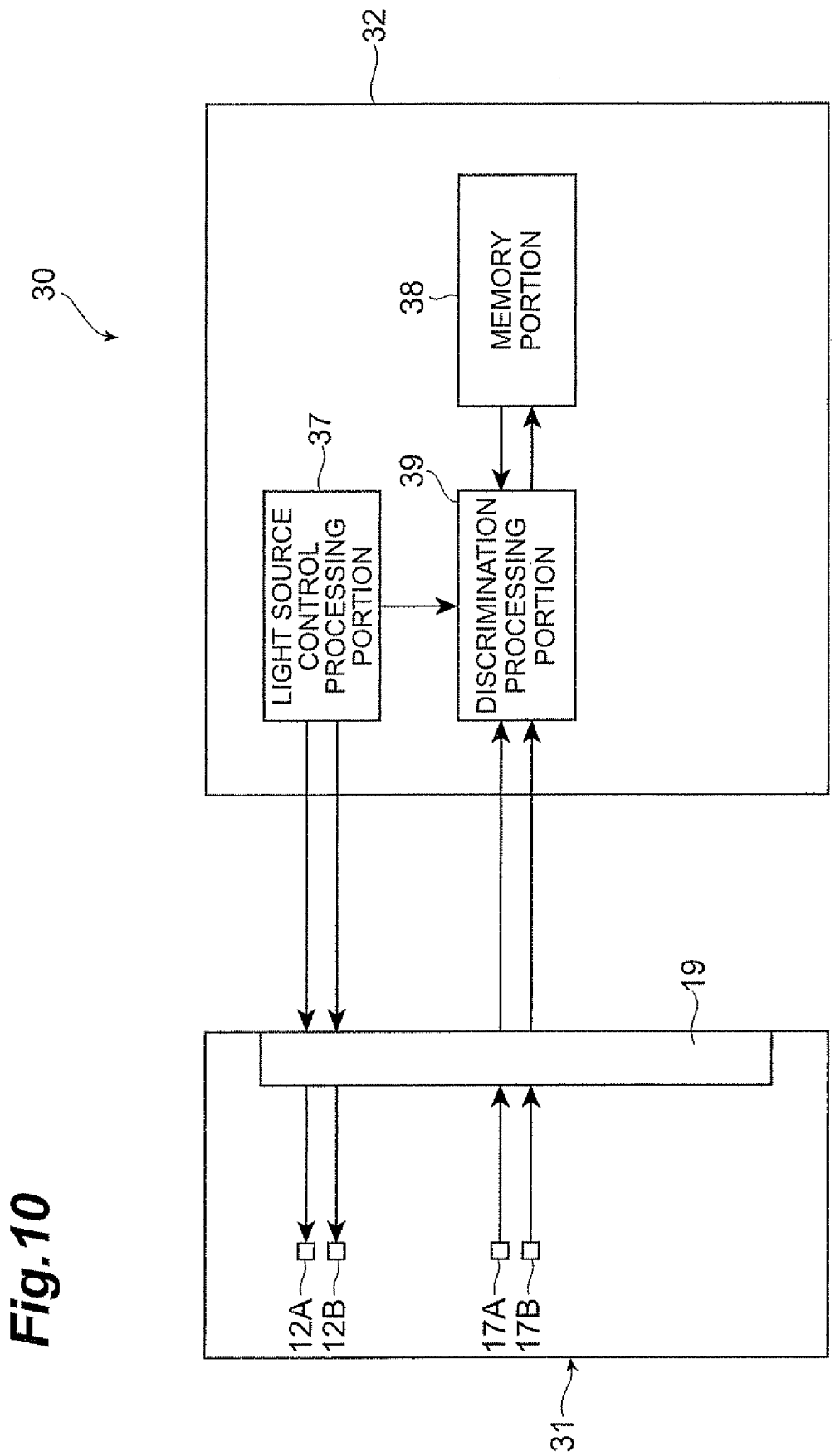
FIG. 10 is a diagram showing functional blocks in a control unit shown in FIG. 7.
Figure 11:
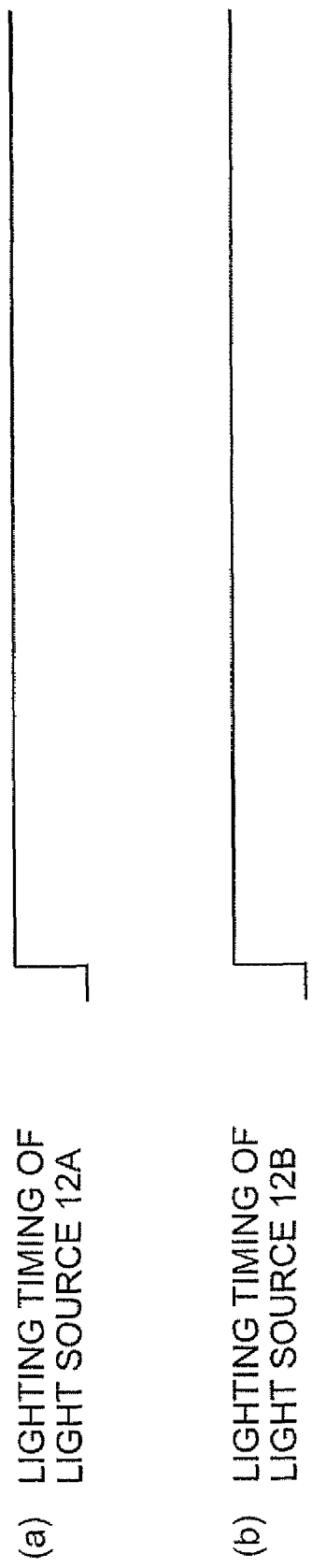
FIG. 11 is a chart showing lighting timings of two light sources shown in FIG. 8.

The control unit 32, as shown in FIG. 10, has a light source control processing portion 37 (an element constituting an illumination portion), a memory portion 38, and a discrimination processing portion 39 (discriminating means). When a banknote arrival sensor (not shown) detects arrival of a banknote 3 passing on the conveyance path 2, at the area near the aperture 4a of the upper conveyance guide plate 4, the light source control processing portion 37 controls a light source driving circuit (not shown) constituting a lighting control portion, so as to keep the light sources 12A, 12B lighted for a predetermined duration, as shown in FIG. 11.

The reference data for discrimination of banknote is preliminarily stored in the memory portion 38. The reference data to be used is a ratio of output value $P_1$ of photosensor 17A obtained by receiving light upon irradiation with the light from the light source 12A and output value $P_2$ of photosensor 17B obtained by receiving light upon irradiation with the light from the light source 12B (hereinafter referred to as an output ratio of photosensors 17A, 17B), for a plurality of inspection regions in the longitudinal direction of banknote 3. The reference data of the output ratio of photosensors 17A, 17B is obtained from output values of photosensors 17A, 17B obtained by conveying a real banknote 3 on the conveyance path 2 and simultaneously receiving light during the simultaneous lighting of the light sources 12A, 12B.

Figure 12:
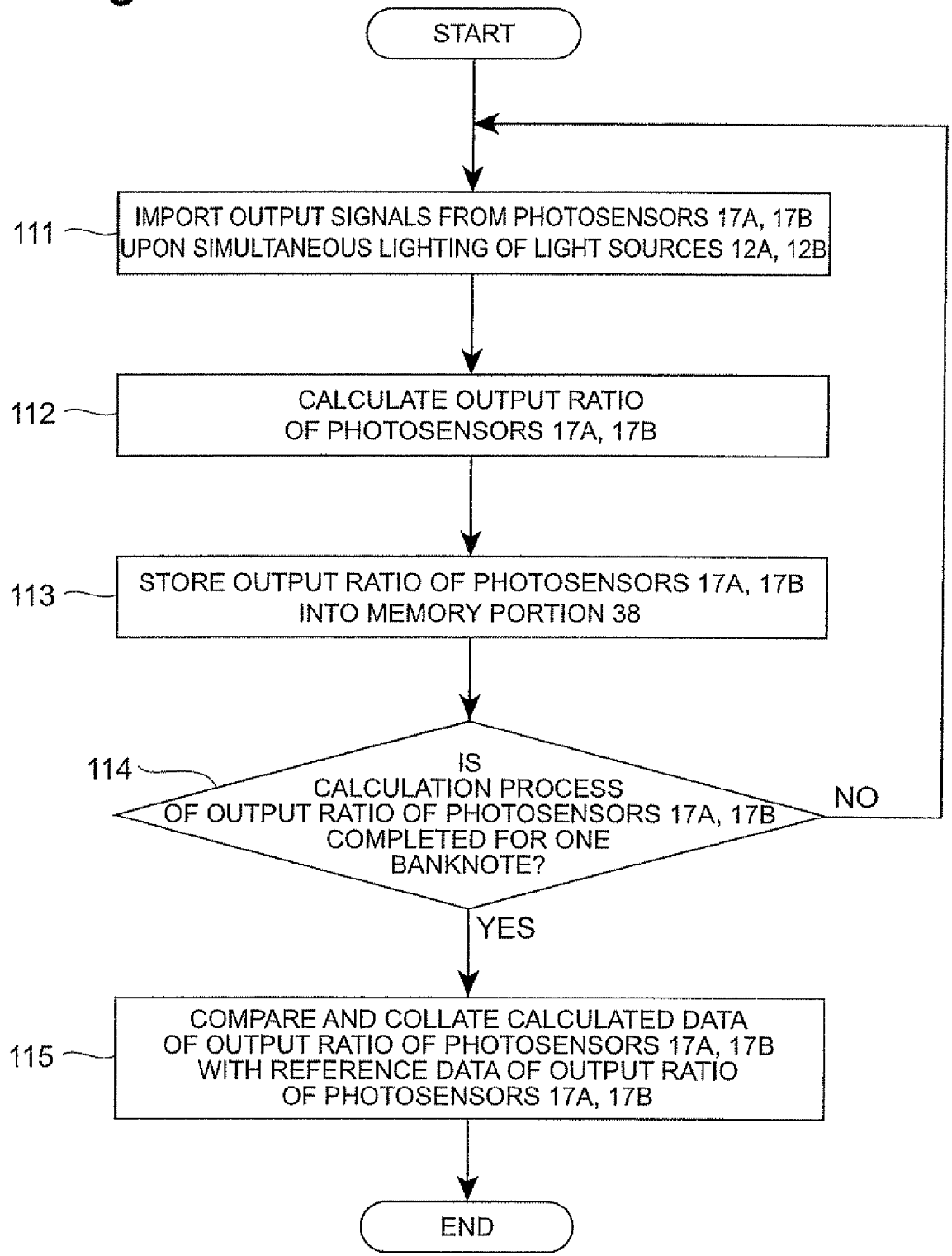
FIG. 12 is a flowchart showing a detailed processing procedure of a discrimination processing portion shown in FIG. 10.

The discrimination processing portion 39 imports the output signals from the photosensors 17A, 17B, performs a predetermined operation, and discriminates the banknote 3 with the use of the reference data for discrimination of banknote stored in the memory portion 38. The detailed processing procedure of the discrimination processing portion 39 is shown in FIG. 12.

As shown in the drawing, the light sources 12A, 12B are first simultaneously lighted to illuminate the banknote 3 under conveyance with light, and the discrimination processing portion 39 imports detection signals of photosensors 17A, 17B obtained by receiving light at the same timing upon the irradiation (step 111). Subsequently, the discrimination processing portion 39 calculates the output ratio of photosensors 17A, 17B from the detected value $P_1$ of photosensor 17A and the detected value $P_2$ of photosensor 17B at this time (step 112), and stores it into the memory portion 38 (step 113). Subsequently, the discrimination processing portion 39 determines whether the output ratio of photosensors 17A, 17B has been calculated for all the inspection regions of one banknote 3 (step 114). When the output ratio of photosensors 17A, 17B is calculated for all the inspection regions, the discrimination processing portion 39 compares and collates each calculated data with the reference data to determine the authenticity and denomination of banknote 3 (step 115).

In the present embodiment, as described above, the output ratio of photosensors 17A, 17B is determined from the output values of photosensors 17A, 17B obtained by receiving light at the same timing during the simultaneous lighting of the light sources 12A, 12B, and the banknote 3 is discriminated using it. Therefore, as in the case of the first embodiment, the apparatus is able to correctly determine the two types of characteristic patterns for security or the like given to the banknote 3 and to perform the discrimination without being affected by the conveyance fluttering of banknote 3 or the like. This improves the accuracy of recognition of banknote 3 and enables the apparatus to adequately discriminate high-accuracy counterfeit banknotes.

Since the apparatus is configured to use the two photosensors 17A, 173 and to keep the light sources 12A, 12B simultaneously lighted for the predetermined duration, it is feasible to reduce influence of noise occurring upon lighting of the light sources 12A, 12B and to stabilize the amount of emission of light from the light sources 12A, 12B. It is also feasible to simplify control of lighting of the light sources 12A, 12B.

Figure 13:
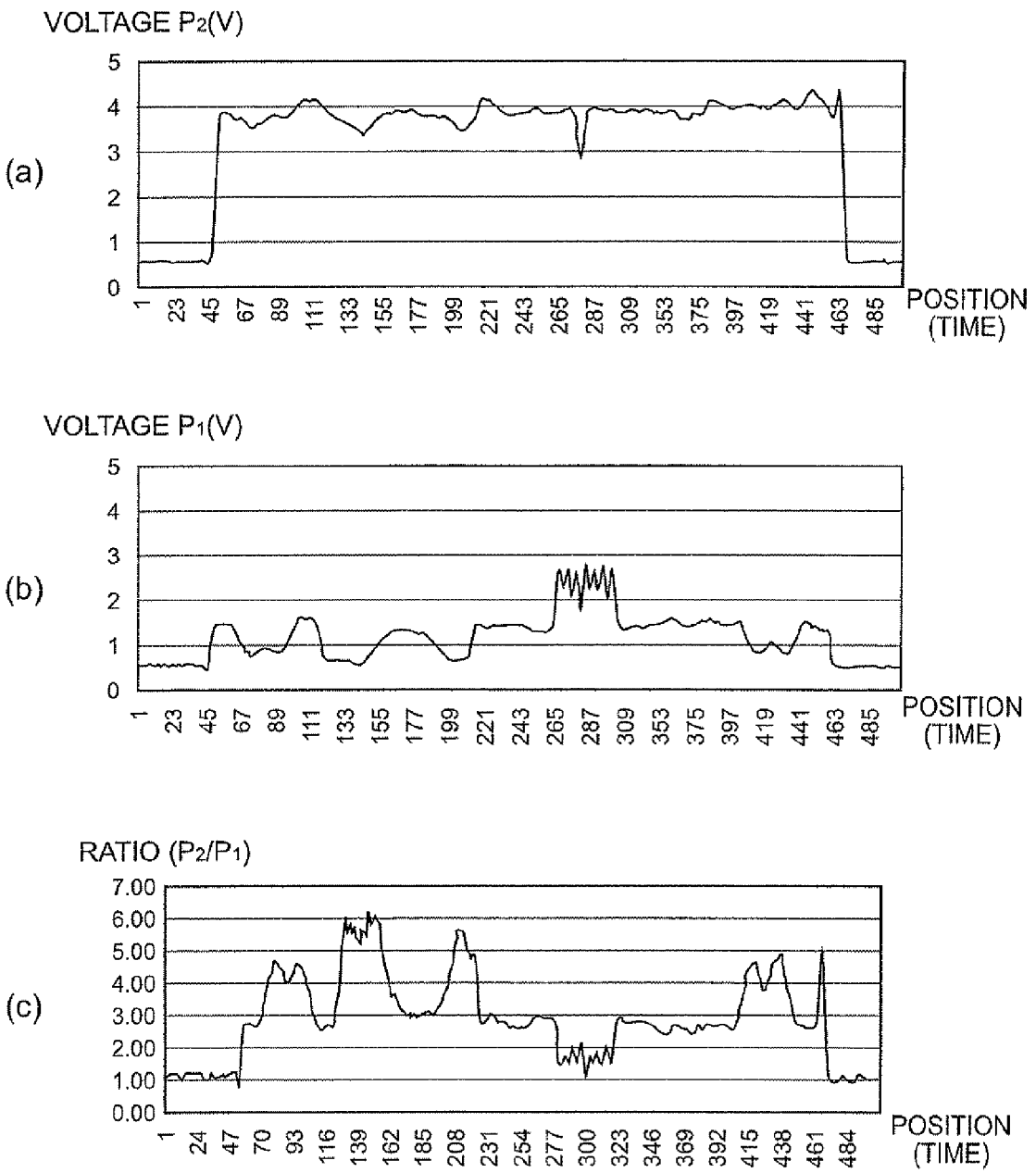
FIG. 13 is a drawing showing an example of output data from photosensors actually obtained by receiving light upon irradiation of a banknote with light from two light sources, and an example of output ratio data from the photosensors.

FIG. 13 (a) shows an example of output data of photosensor 17B upon actual irradiation of banknote 3 with the infrared light from the light source 12B, and FIG. 13 (b) shows an example of output data of photosensor 17A upon actual irradiation of banknote 3 with the ultraviolet light from the light source 12A. FIG. 13 (c) shows data of the output ratio of photosensors 17A, 17B obtained from the output data of the photosensors 17A, 17B shown in FIGS. 13 (a) and (b). By using such output ratio data of photosensors 17A, 17B, it becomes feasible to achieve the differentiation process with little influence of conveyance fluttering of banknote 3.

The present invention is by no means limited to the above embodiments. For example, the above embodiments used the output ratio data of the photosensor(s) to perform the discrimination of banknote 3, but it is also possible to use any combined data from the output signals of the photosensor(s) obtained by receiving light within the same period of time upon irradiation of banknote 3 with the light from the light sources 12A, 12B, e.g., output difference data of the photosensor(s) or the like. In this case, the characteristic patterns or the like provided on the banknote 3 can also be accurately determined by comparing and collating the combined data obtained, with the reference data, so that the accuracy of recognition of banknote 3 can be improved.

The above embodiments used the two light sources 12A, 12B for emitting the light beams in different wavelength bands, but the present invention does not have to be limited particularly to this example, and may be applied to use of three or more light sources. For example, where visible light is used as a light source, it becomes feasible to collect data of details of a banknote according to the light source to be used.

Figure 14:
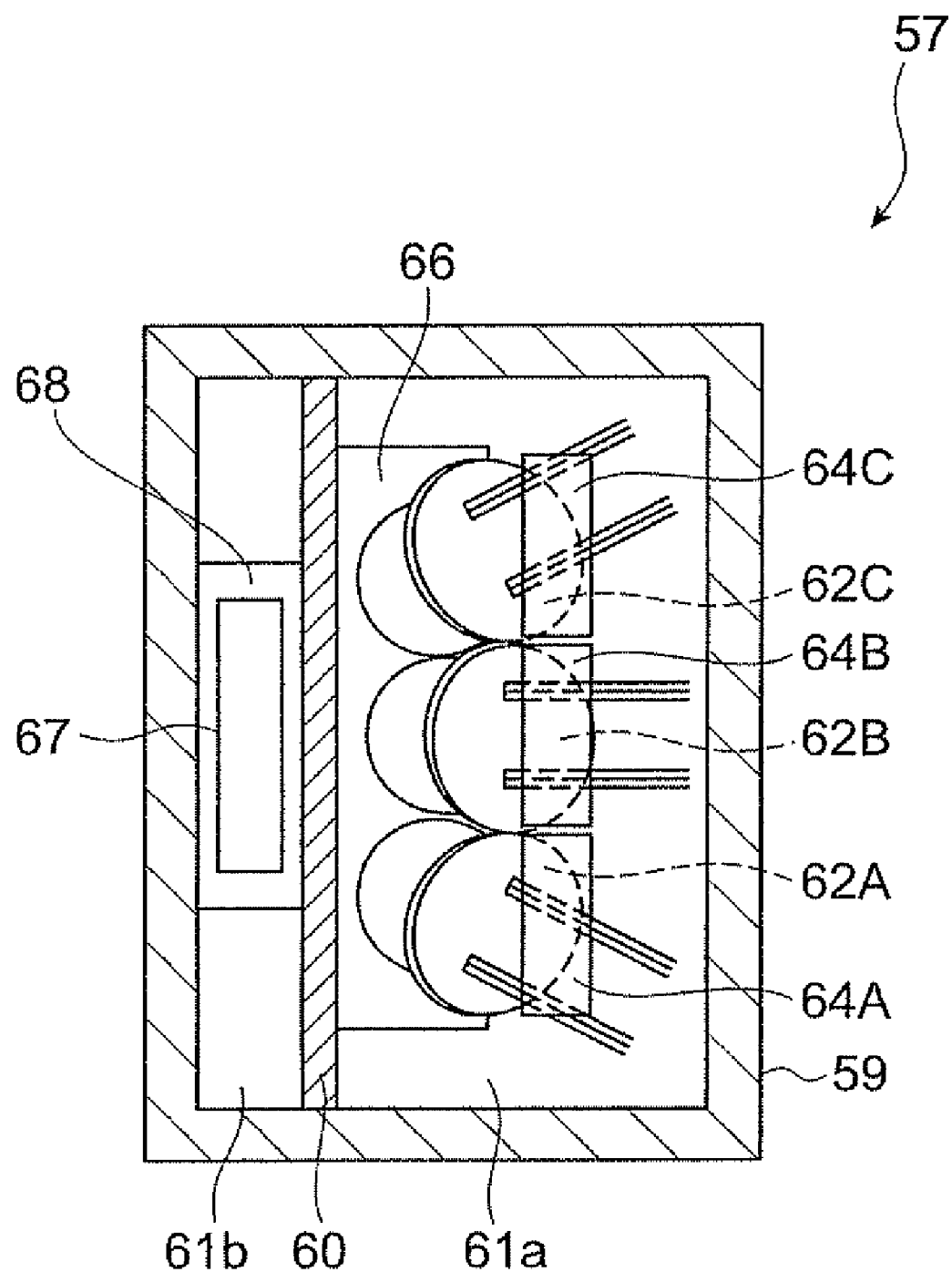
FIG. 14 is a horizontal sectional view of a housing in an inspection device of another embodiment.

FIG. 14 is a drawing showing an embodiment in which a green LED as a third light source is incorporated in the sensor unit of the inspection device, in addition to the aforementioned ultraviolet LED and infrared LED as light sources.

The sensor unit 57 shown in FIG. 14 has a configuration similar to the sensor unit 7 shown in FIGS. 1 and 2, and can be incorporated instead of the sensor unit 7 in the inspection device 1. The sensor unit 57 has a housing 59 of approximately rectangular parallelepiped shape and a partition 60 extending in the direction of height of the inspection device is provided in the housing 59. The three light sources 62A, 62B, 62C are accommodated in one space 61a of the housing 57 formed by the partition 60. The light source 62A is an ultraviolet LED for generating light containing the ultraviolet component, the light source 62B is an infrared LED for generating light containing the infrared component, and the light source 62C is a green LED for generating green light. Monitor photosensors 64A, 64B, and 64C, which monitor the quantity of light emitted from the light sources 62A, 62B, 62C, are mounted on a printed circuit board (not shown) provided on the upper surface portion of the housing 57. In order to prevent light from being reflected on the surface of the banknote and becoming unwanted noise, an optical filter 66 capable of removing an unwanted light component is disposed on the lower surface portion of the housing 57.

A photosensor 67 for detection and an optical filter 68 are accommodated in the other space 61b of the housing 57 formed by the partition 60. The photosensor 67 receives light generated from the surface of the banknote upon irradiation of the surface of the banknote with the light from the light sources 62A, 62B, 62C, and is fixed on the aforementioned printed circuit board (not shown). The optical filter 68 is a filter for removing an unwanted light component for the photosensor 67 among the light generated from the surface of the banknote.

It is noted that the optical filters 66, 68 are not particularly essential components in the sensor unit 57.

The sensor unit 57 shown in FIG. 7 has the configuration similar to the sensor unit 7 in the first embodiment shown in FIG. 2, except that the sensor unit 57 has the light source 62C of the green LED and the monitor photosensor 64C for monitoring the quantity of light emitted from the light source 62C and is different in the functions of the filters 16, 18. For this reason, when the light source processing portion 20 of the control unit 8 shown in FIG. 3 is arranged to perform the processing corresponding to the light source 62C, the inspection device is able to determine the authenticity and denomination of banknote 3 passing on the conveyance path 2, as the inspection device of the first embodiment was.

As described above, when the green LED is used as the third light source, the output data from the photosensor upon irradiation with the green light is also added to the determination of the banknote. Accordingly, it becomes feasible to perform more accurate recognition of the banknote. The green LED provides high contrast for each of colors of printed patterns on banknotes among the visible light and is relatively inexpensive and high in luminance among short-wavelength LEDs; therefore, it is suitable for the third light source.

The sensor unit provided with the three light sources like the sensor unit 57 may be modified in a configuration wherein three photosensors are provided and separated by partitions between them so as to separately receive respective lights generated from the surface of the banknote, like the sensor unit 31 of the inspection device 30 of the second embodiment (see FIGS. 7, 8, and 9).

The above embodiments used the plurality of light sources, but it is also possible to use one light source for emitting light containing a plurality of wavelength bands, such as a white light source, as a light source.

Furthermore, the above embodiments were directed to inspection of banknotes, but the inspection device of the present invention is not limited particularly to the banknotes, and is also applicable to inspection objects such as chits, stock certificates, and cards.

INDUSTRIAL APPLICABILITY

The present invention enables accurate recognition of the authenticity or the like of an object passing on the conveyance path. This makes it feasible to adequately discriminate highly accurately forged objects.

The invention claimed is:

1. An inspection device for inspecting an object passing on a conveyance path, comprising:
    an upper conveyance guide plate and a lower conveyance guide plate defining the conveyance path and separated by a clearance in a range from about 2 mm to about 3 mm;
    an illumination portion illuminating the object with light in a plurality of wavelength bands;
    at least one light-receiving and detecting element detecting light from the object; and
    a discrimination processing portion discriminating the object by combining data from a plurality of detection signals obtained by the light-receiving and detecting element which detects the light from the object substantially within an identical period of time when the illuminating portion illuminates the object with the light in the plurality of wavelength bands, and by comparing and collating combined data with preset reference data, wherein the discrimination processing portion obtains, as the combined data, a ratio of a plurality of detected values obtained by the light-receiving and detecting element which detects the light from the object substantially within an identical period of time when the illuminating portion illuminates the object, while in the conveyance path, with the light in the plurality of wavelength bands.

2. The inspection device according to claim 1, wherein the illumination portion includes a plurality of light sources emitting light beams in different wavelength bands, and a lighting control portion controlling each of the light sources while individually switching the light sources.

3. The inspection device according to claim 2, wherein the plurality of light sources includes a first light source emitting ultraviolet light, and a second light source emitting infrared light.

4. The inspection device according to claim 3, including an ultraviolet removing filter disposed between the conveyance path and the light-receiving and detecting element and removing the ultraviolet light emitted from the first light source.

5. The inspection device according to claim 4, including an ultraviolet-infrared transmitting filter disposed between the conveyance path, the first light source, and the second light source, and removing a visible light component from the ultraviolet light emitted from the first light source and transmitting the infrared light emitted from the second light source.

6. The inspection device according to claim 3, including an ultraviolet-infrared transmitting filter disposed between the conveyance path, the first light source, and the second light source, and removing a visible light component from the ultraviolet light emitted from the first light source and transmitting the infrared light emitted from the second light source.

7. The inspection device according to claim 2, wherein the plurality of light sources includes a first light source emitting ultraviolet light, a second light source emitting infrared light, and a third light source emitting green light.

8. The inspection device according to claim 1, wherein the illumination portion includes a plurality of light sources emitting respective light beams in different wavelength bands, and including a plurality of light-receiving and detecting elements separately located for detecting light from the object in correspondence to respective light sources when the object is illuminated with the light beams from the respective light sources.

9. The inspection device according to claim 8, further comprising optical filters, each optical filter being disposed between the conveyance path and a respective light-receiving and detecting element, each filter transmitting only a certain light component among light components with a plurality of features from the object when the object is illuminated with the light from each light source.

10. The inspection device according to claim 9, wherein the plurality of light sources includes a first light source emitting ultraviolet light, and a second light source emitting infrared light.

11. The inspection device according to claim 9, wherein the plurality of light sources includes a first light source emitting ultraviolet light, a second light source emitting infrared light, and a third light source emitting green light.

12. The inspection device according to claim 8, wherein the plurality of light sources includes a first light source emitting ultraviolet light, and a second light source emitting infrared light.

13. The inspection device according to claim 8, wherein the plurality of light sources includes a first light source emitting ultraviolet light, a second light source emitting infrared light, and a third light source emitting green light.

* * * * *